United States Patent [19]

Shaber et al.

[11] Patent Number: 5,252,594
[45] Date of Patent: Oct. 12, 1993

[54] FUNGICIDAL (2-ARYL-2-SUBSTITUTED)ETHYL-1,2,4-TRIAZOLES

[75] Inventors: Steven H. Shaber, Horsham, Pa.; Katherine E. Flynn, Loveland, Ohio

[73] Assignee: Rohm and Haas Company, Philadelphia, Pa.

[21] Appl. No.: 900,047

[22] Filed: Jun. 17, 1992

[51] Int. Cl.$^5$ ............... A01N 43/653; C07D 249/08
[52] U.S. Cl. ................... 514/383; 514/184; 548/101; 548/267.2; 548/267.4; 548/267.6
[58] Field of Search ............ 514/383, 184; 548/267.2, 267.4, 267.6, 101

[56] References Cited

U.S. PATENT DOCUMENTS

| | | | |
|---|---|---|---|
| 4,366,165 | 12/1982 | Miller et al. | 424/269 |
| 4,398,942 | 8/1983 | Ikari et al. | 71/92 |
| 4,598,085 | 7/1986 | Heeres et al. | 514/383 |
| 4,622,335 | 11/1986 | Kramer et al. | 514/383 |

FOREIGN PATENT DOCUMENTS

| | | | |
|---|---|---|---|
| 1189857 | 7/1985 | Canada | 548/267.2 |
| 61798 | 10/1982 | European Pat. Off. | |
| 2104065 | 3/1983 | United Kingdom | |

*Primary Examiner*—Patricia L. Morris
*Attorney, Agent, or Firm*—Clark R. Carpenter; Terence P. Strobaugh

[57] ABSTRACT

This invention relates to novel (2-aryl-2-substituted)ethyl-1,2,4-triazoles and the enantiomorphs, acid addition salts and metal salt complexes thereof, as well as their method of preparation and their use as highly active broad-spectrum systemic fungicides.

10 Claims, No Drawings

FUNGICIDAL (2-ARYL-2-SUBSTITUTED)ETHYL-1,2,4-TRIAZOLES

BACKGROUND OF THE INVENTION

1) Field of the Invention

This invention relates to (2-aryl-2-substituted)ethyl-1,2,4-triazoles, their enantiomorphs, acid addition salts and metal salt complexes, compositions containing these compounds and the use of these compounds as fungicides, particularly against phytopathogenic fungi.

2) Description of Related Art

U.S. Pat. No. 4,366,165, discloses 1- and 4-aryl-cyanoalkyl-1,2,4-triazoles as fungicidal agents. The compounds of this disclosure are limited to those having a cyano group bonded to the beta carbon of the alkyl substituent on the triazole.

European Patent Application No. 61,798 discloses 2-ethyltriazole derivatives having a phenyl substituent on the beta carbon of the ethyl group. All of the compounds of this disclosure also have a hydrogen atom attached to the beta carbon as well as a secondary or tertiary amino group.

European Patent Application No. 52,424 discloses 2-ethyl substituted triazole compounds in which the beta carbon of the ethyl group has a chloro, cyano, or oxy substituent.

U.K. Patent Application No. GB 2104065A discloses microbial mandelic acid derivatives and mandelonitriles. These compounds are generally 2-ethyltriazoles in which the beta carbon of the ethyl group is substituted by an aromatic substituent, an oxy substituent, and a carboxyl or cyano group. All of the compounds of this disclosure require that at least one of the substituents on the beta carbon of the ethyl group be an oxy substituent.

U.S. Pat. No. 4,622,335 discloses fungicidal hydroxyethylazolyl-oxime derivatives. The compounds of this disclosure, in addition to having the oxime functionality on the asymmetric carbon, also all have a hydroxy group on the same carbon.

U.S. Pat. No. 4,598,085 discloses fungicidal 1-(2-aryl-2-R-ethyl)-1H-1,2,4-triazoles as fungicidal agents. The compounds of this disclosure all have a hydrogen atom on the beta carbon of the ethyl substituted triazole in addition to an optionally substituted phenyl group and lower alkyl, cycloalkyl, lower alkenyl, aryl methyl and aryl ethyl substituents.

German Patent Publication 3408127 discloses fungicidal N-(azolylethyl)carboxamides. The compounds of this disclosure reportedly have a carboxamide group attached to the beta carbon of the ethyl substituent of the triazole.

U.S. Pat. No. 4,398,942 discloses herbicidally active phenylacetonitriles. These compounds, while being substituted ethyl-triazoles, have either a cyano or ethynyl group on the beta carbon of the ethyl substituent.

SUMMARY OF THE INVENTION

This invention relates to novel (2-aryl-2-substituted)ethyl-1,2,4-triazoles, the enantiomorphs, acid addition salts and metal salt complexes thereof, and their use as highly active broad-spectrum systemic fungicides. In particular, this invention relates to compounds of the formula

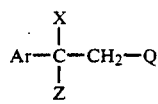

wherein X is —NC, —CH$_2$N≡C, —CHO, —CON$_3$, —CH=NOR, —CH$_2$NHCHO, —NHCO$_2$R, —NHCONHR, —CH=C(R)$_2$, —NH$_2$, —NHCHO, —NHCOCH$_3$, —N=C(R)$_2$, —NCO, —NO$_2$, or

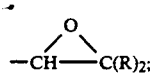

R is independently hydrogen, lower alkyl, phenethyl, benzyl, or phenyl; Ar is an optionally substituted aryl group; Z is alkyl, haloalkyl, cycloalkyl, aryl, cycloalkylalkyl or aralkyl; Q is a 1-(1,2,4-triazolyl) or a 4-(1,2,4-triazolyl); and the agronomically acceptable enantiomorphs, acid addition salts and metal salt complexes thereof.

DETAILED DESCRIPTION OF THE INVENTION

This invention relates to novel (2-aryl-2-substituted)ethyl-1,2,4-triazoles and the enantiomorphs, acid addition salts and metal salt complexes thereof, as well as their use as highly active broad-spectrum systemic fungicides. In particular, this invention relates to compounds of the formula

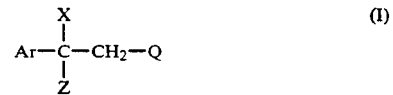

wherein Ar is optionally substituted aryl, such as phenyl, naphthyl, pyridyl, thienyl or furyl;

Z is (C$_2$–C$_{12}$)alkyl, haloalkyl, cycloalkyl, cycloalkylalkyl, aryl, or aralkyl;

Q is a triazolyl; and

X is —NC, —CH$_2$N≡C, —CHO,—CON$_3$, —CH=NOR, —CH$_2$NHCHO, —NHCHO, —NHCOCH$_3$, —NHCO$_2$R, —NHCONHR, —NH$_2$, —CH=CR$_2$, —N=CR$_2$, —NCO, —NO$_2$, or

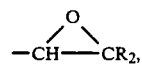

wherein R is hydrogen or lower alkyl; and the agronomically acceptable enantiomorphs, acid addition salts, and metal salt complexes thereof.

The term "alkyl" includes both branched and straight chained alkyl groups of from 1 to 12 carbon atoms. Typical alkyl groups are methyl, ethyl, propyl, isopropyl, n-butyl, sec-butyl, isobutyl, tert-butyl, pentyl, neopentyl, isopentyl, hexyl, heptyl, isooctyl, nonyl, decyl, isodecyl, undecyl, dodecyl and the like. "Lower alkyl" means C$_1$–C$_5$ alkyl.

The term "haloalkyl" refers to an alkyl group substituted with 1 to 3 halogen atoms. The term "alkoxy" refers to an alkoxy group, straight or branched, having a chain length of 1 to 12 carbon atoms. The term "haloalkoxy" refers to an alkoxy group substituted with 1 to 3 halogen atoms. The term "alkenyl" refers to an ethylenically unsaturated hydrocarbon group, straight or branched, having a chain length of 2 to 12 carbons and 1 or 2 ethylenic bonds. The term "haloalkenyl" refers to an alkenyl group substituted with 1 to 3 halo atoms. The term "alkynyl" refers to an alkynyl group, straight or branched, having a chain length of 2 to 12 carbon atoms and 1 to 2 acetylenic bonds. The term "cycloalkyl" refers to a saturated ring system having 3 to 8 carbon atoms. The term "cycloalkenyl" refers to an unsaturated ring system of 5 to 8 carbon atoms, having 1 or 2 ethylenic bonds. The term "cycloalkylalkyl" refers to a cycloalkyl substituted with a lower alkyl, as defined above.

By the term "aryl" is meant an aromatic ring selected from phenyl, naphthyl, pyridyl, thienyl or furyl, preferably a phenyl or naphthyl group which is optionally substituted with up to three substituents, preferably with up to two substituents, selected from the group consisting of halogen, trihalomethyl, phenyl, phenoxy, optionally halo-substituted ($C_1$ to $C_4$)alkyl and ($C_1$ to $C_4$) alkoxy.

Typical aryl substituents include, but are not limited to, phenyl, naphthyl, 4-chlorophenyl, 4-fluorophenyl, 4-bromophenyl, 2-methoxyphenyl, 2,4-dibromophenyl, 3,5-difluorophenyl, 2,4,6-trichlorophenyl, 2,3,4-tribromophenyl, 3,4-dichlorophenyl, 2-chloro-4-iodophenyl, 3,4,5-trimethylphenyl, 4-methoxyphenyl, 2-chloronaphthyl, 2,4-dimethoxyphenyl, 4-(trifluoromethyl)phenyl, 2,4-diiodonaphthyl, 2-iodo-4-methylphenyl, 2-, 3-or 4-pyridine, 2- or 3-thiophene, 2- or 3-furan, and the like.

The term "aralkyl" is used to define a group wherein the alkyl chain is from 1 to 5 carbon atoms and can be branched or straight chained, preferably the latter, and the aryl portion of the group is meant to be defined as above. Typical aralkyl substituents include, but are not limited to, 2,4-dichlorobenzyl, 2,4-dibromobenzyl, 2,4,6-trichlorobenzyl, 3,5-dimethoxyphenethyl, 2,4,5-trimethylphenbutyl, 2,4-dibromonaphthylbutyl, 2,4-dichlorophenethyl and the like.

In the definition of Q, the term "optionally substituted 1-(1,2,4-triazolyl) or 4-(1,2,4-triazolyl)" is meant to include unsubstituted 1- and 4-(1,2,4-triazolyl) and 1- and 4-(1,2,4-triazolyl) which can be substituted with up to two substituents selected from halo or ($C_1$ to $C_4$)alkyl.

A preferred embodiment of this invention is the compounds, enantiomorphs, salts and complexes of Formula (I) wherein Ar is phenyl or phenyl substituted with up to three substituents, preferably with up to two substituents independently selected from halo, trihalomethyl, preferably trifluoromethyl, cyano, ($C_1$-$C_4$)alkyl, ($C_1$-$C_4$)alkoxy, or phenyl; Z is selected from ($C_2$ to $C_{12}$)alkyl, ($C_1$-$C_{12}$)haloalkyl, ($C_3$ to $C_8$)cycloalkyl, ($C_3$ to $C_8$)cycloalkyl($C_1$ to $C_5$)alkyl, unsubstituted phenyl, benzyl or phenethyl, or phenyl, benzyl or phenethyl, the aromatic ring which is substituted with up to two halo atoms or trihalomethyl; Q is an unsubstituted 1-(1,2,4-triazole); and R is H or ($C_1$ to $C_4$)alkyl.

A more preferred embodiment of this invention is the compounds, enantiomorphs, salts and complexes of Formula (I) wherein Ar is phenyl, or phenyl substituted at the 4-position with chloro, bromo, fluoro, or trifluoromethyl; Z is ($C_2$ to $C_6$)alkyl, phenyl, benzyl or phenethyl, or monochloro substituted phenyl, benzyl or phenethyl; Q is 1-(1,2,4-triazole); and R is H.

Typical compounds encompassed by the present invention include:

N-{2-(4-chlorophenyl)-2-[(1,2,4-triazol-1-yl)methyl]-hexyl}formamide;

2-(4-chlorophenyl)-2-[(1,2,4-triazol-1-yl)methyl]hexylisocyanide;

2-(4-chlorophenyl)-2-[1,2,4-triazol-1-yl)methyl]hexanal;

3-(4-chlorophenyl)-3-[1,2,4-triazol-1-yl)methyl]-1-heptene;

2-(4-chlorophenyl)-(E,Z)-1-hydroxyamino-2-[(1,2,4-triazol-1-yl)methyl]hexanal;

2-(4-chlorophenyl)-2-[(1,2,4-triazol-1-yl)methyl]hexanoylazide;

2-(4-chlorophenyl)-1-(1,2,4-triazol-1-yl)-2-hexylamine;

N-[2-(4-chlorophenyl)-1-(1,2,4-triazol-1-yl)-2-hexyl]formamide;

2-(4-chlorophenyl)-1-(1,2,4-triazol-1-yl)-2-hexylisocyanide; and

N-[2-(4-chlorophenyl)-1-(1,2,4-triazol-1-yl)-2-hexyl]acetamide.

The compounds described herein were synthesized in three cascading syntheses starting from the arylcyanoethyl-1,2,4-triazoles the synthesis of which is described in Miller, U.S. Pat. No. 4,366,165, the disclosure of which is incorporated by reference herein.

Procedures used in the cascade synthesis are well known to those or ordinary skill in the art. These syntheses are described, for example, in Jerry March, *Advanced Organic Chemistry: Reactions, Mechanism and Structure*, John Wiley and Sons, 1985; hereinafter "March".

The cyano group of the arylcyanoethyl-1,2,4-triazoles of Miller, U.S. Pat. No. 4,366,165, may be hydrolyzed to the corresponding carboxylic acid under strongly acidic conditions, for example, concentrated hydrochloric, hydrobromic or 50% sulfuric acid, at temperatures of about 100°-140° C., March, p. 788. The acid may in turn be reduced to the alcohol using a suitable reducing agent, such as lithium aluminum hydride in a suitable inert solvent at temperatures of about −20° to 10° C., March p. 1099. Alternatively, the cyano group is reduced to an amine with a suitable reducing agent such as lithium aluminum hydride in an inert solvent such as ether or tetrahydrofuran, March p. 815.

The acid, the alcohol, and the amine are used to obtain the novel fungicides of this invention. Examples of the preparation of the starting acid, alcohol and amine are shown in Examples A-D below.

The 2-substituted-2-aryl-2-[(1,2,4-triazol-1-yl)methyl]ethan-1-ols are oxidized to the aldehydes in the first cascade using oxidizing agents such as chromium based oxidants for example, chromium trioxide/pyridine in chloroform, March p. 1057. The aldehydes in turn are used to obtain three further derivatives: oximes, oxime ethers, and alkylenes. Treatment of the aldehyde with hydroxylamine hydrochloride or alkoxyamine hydrochlorides affords the oxime or oxime ether, March p. 359, p. 805. Addition of the ylid derived from an alkyl(-triphenyl)phosphonium bromide to the aldehyde gives an alkylene, after purification by flash chromatography, March p. 845. The alkylene may be converted to the epoxide by treatment with any of a variety of peracids, for example, meta-chloroperbenzoic acid, March p. 735. The alkylene may also be halogenated and then dehydrohalogenated to obtain the alkyne.

The second cascase is initiated with a 2-substituted 2-aryl-2-[(1,2,4-triazol-1-yl)methyl]ethylamine. Addition of this amine to the mixed anhydride formed in situ from acetic anhydride and formic acid yields the methylenoformamide. Dehydration of the methylenoformamide at room temperature with 3-ethyl-2-chlorobenz-oxazolium tetrafluoroborate affords the methylene isocyanide after flash chromatography, March p. 934.

The third cascade starts with a 2-substituted-2-aryl-2-[1,2,4-triazol-1-yl)methyl]acetic acid. Treatment with diphenylphosphorylazide and triethylamine at room temperature for about 15 hours gives the carbonyl azide. Heating of the carbonyl azide in a non-alcoholic solvent affords the isocyanate, March p. 984. When the same reaction is run at reflux for 48 hours the amine is obtained. Treatment of the amines with various acid chlorides or acetic anhydride gives amides. The amines may also be converted to carbamates or ureas. Finally, the oxidation of the amine with a peracid yields a nitrotriazole. The formamide may be dehydrated to the isocyanide as above.

The above reactions are illustrated in Examples 1–10, below. Another embodiment of this invention comprises the metal salt complexes of the formula

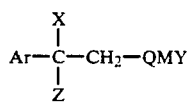

II wherein Ar, Z, Q and X are as defined in Formula (I) above and M is a cation selected from Group IIA, IB, IIB, IVA, VIB, VIIB, and VIII of the Periodic Table and Y is an anionic counterion selected in such a manner that the sum of the valence charges of the cation M and anion Y equals zero.

Typical cations of the metal salt complexes of this invention are magnesium, manganese, copper, nickel, zinc, iron, cobalt, calcium, tin, cadmium, mercury, chromium, lead, barium and the like.

Typical anions encompassed by this invention are chloride, bromide, iodide, fluoride, sulfate, bisulfate, perchlorate, nitrate, nitrite, phosphate, carbonate, bicarbonate, acetate, citrate, oxalate, tartarate, malate, maleate, fumarate, p-toluenesulfonate, methanesulfonate, mono or di($C_1$ to $C_4$)alkyldithiocarbamate, ($C_1$ to $C_4$)alkylene-bisdithiocarbamate, and the like.

The acids which can be utilized in making the acid addition salts of the present invention include hydrochloric, hydrobromic, nitric, sulfuric, phosphoric, hydroiodic, hydrofluoric, perchloric, p-toluenesulfonic, methanesulfonic, acetic, citric, tartaric, malic, maleic, oxalic, fumaric, phthalic and the like.

The acid addition salts of the 1,2,4-triazoles of this invention can be prepared by standard techniques well-known in the art. For example, the 1,2,4-triazole of Formula (II) can be dissolved in an appropriate solvent such as diethyl ether, tetrahydrofuran, ethanol, methanol, and the like or combinations thereof, and treated with an equivalent or excess amount of a mineral or organic acid which may or may not be dissolved in an appropriate solvent. The mixture is then either cooled or evaporated to give the salt which can either be used as such or recrystallized from an appropriate solvent or combination of appropriate solvents.

The metal salt complexes of the above 1,2,4-triazoles can be prepared by adding dropwise, with stirring, a stoichiometric amount of a metal salt dissolved in an appropriate solvent or combination of solvents. The reaction mixture is briefly stirred and the solvent is removed under reduced pressure to give the metal salt complex of the 1,2,4-triazoles of Formula (II).

The metal salt complexes can also be prepared by mixing stoichiometric or excess amounts of the metal salt and a triazole of Formula (I) in the desired amount of solvent containing the appropriate adjuvants just prior to spraying the plants. Adjuvants that may be included in this in situ preparation may be detergents, emulsifiers, wetting agents, spreading agents, dispersing agents, stickers, adhesives, and the like which are used in agricultural applications.

Solvents that can be utilized in these procedures include any polar solvent for example, water, methanol, ethanol, isopropanol or ethylene glycol and any aprotic dipolar solvent, for example, dimethyl sulfoxide, acetonitrile, dimethylformamide, nitromethane or acetone.

The metal cations that can be used in these procedures can be selected from the group consisting of calcium, magnesium, manganese, copper, nickel, zinc, iron, cobalt, tin, cadmium, mercury, chromium, lead, barium and the like.

Any appropriate anion, for example, chloride, bromide, iodide, sulfate, bisulfate, phosphate, nitrate, perchlorate carbonate, bicarbonate, hydrosulfide, hydroxide, acetate, oxalate, malate, citrate and the like may be utilized as the counterion in the metal salt.

The compounds of this invention possess an asymmetric carbon atom and thus exist as racemic mixtures. The d and l enantiomorphs in these racemic mixtures can be separated via standard techniques such as fractional crystallization with d-tartaric acid, l-tartaric acid, l-quinic acid and the like followed by basification and extraction of the d or l enantiomorph free base.

The following examples are provided to illustrate the methods of preparation of the intermediates and compounds of the present invention.

EXAMPLE A 2-4(4-chlorophenyl)-2-[(1,2,4-triazol-1-yl)methyl]hexanoic acid

A mixture of 60.0 grams (g) (0.208 mole) of alpha-n-butyl-alpha-(4-chlorophenyl)-1H-1,2,4-triazole-1-propanenitrile and 200 milliliters (mL) of 48% hydrobromic acid was stirred at reflux for 96 hours after which GLC indicated disappearance of the starting material. The reaction was diluted with ethyl ether and extracted with water until pH neutral. The ether was extracted with sufficient 10% sodium hydroxide to maintain the pH at 14 followed by neutralization with 35% hydrochloric acid at which time a white solid precipitate formed. The solid was collected by filtration and washed with water until the aqueous rinse was neutral. The product was dried under vacuum and gave 49.0 g (76.5% yield) of a white solid, melting point 169°–171° C.

EXAMPLE B 4-(4-Chlorophenyl)-2-[(1,2,4-triazol-1-yl)methyl]butan-1-ol

A slurry of 16 g (0.42 mole) of lithium aluminum hydride in 1000 mL of dry tetrahydrofuran was cooled to 5° C. while stirring under nitrogen; 142 g (0.40 mole) of 2-(4-chlorophenyl)-2-[(1,2,4-triazol-1-yl)methyl]-butanoic acid in 1500 mL of dry tetrahydrofuran was added dropwise over 4 hours maintaining the temperature at 5°–10° C. The mixture was stirred 16 hours at room temperature. The reaction was quenched at 5° C. with the addition of 500 mL of saturated sodium sulfate and the solvent removed under vacuum. The gelatinous solid was filtered with toluene which was washed with 2×1000 mL of water and 1000 mL of saturated sodium chloride solution (brine). The solvent was dried, filtered through Celite ®, concentrated and gave 99 g (72.6% yield) of a viscous yellow glass which slowly crystallized, melting point 40°–45° C.

EXAMPLE C

2-Phenyl-2-[(1,2,4-triazol-1-yl)methyl]-1-hexylamine

To 21 g (0.55 mole) of lithium aluminum hydride was charged 127 g (0.50 mole) alpha-butyl-alpha-phenyl-1H-1,2,4-triazole-1-propanenitrile in 2500 mL of dry ether over 2.5 hours with stirring under nitrogen. The reaction was stirred for an additional 5 hours after which GLC indicated the reaction was complete. The reaction was quenched with sodium sulfate, filtered and the organic phase separated. The aqueous phase was extracted with 1000 mL of ether. The organics were combined, washed with 3×1.5 liters of ice water, dried, filtered and concentrated without external heating and gave 88 g (69.2% yield) of a pale green oil.

EXAMPLE D 4-(4-Chlorophenyl)-2-penyl-2-[(1,2,4-triazol-1-yl)methyl]-1-butylamine A slurry of 18 g (0.45 mole) of lithium aluminum hydride in 1000 mL of dry tetrahydrofuran was cooled to 5° C. while stirring under nitrogen. To the slurry was added alpha-(2-(4-chlorophenyl)ethyl)-alpha-phenyl-1H-1,2,4-triazole-1-propanenitrile in 2000 mL of dry tetrahydrofuran over 3 hours. The reaction was kept at 5°–10° C. during the addition then allowed to warm to room temperature and stirred overnight. The reaction was cooled in an ice bath and quenched with the slow addition of sodium sulfate. The solvent was removed and the residue was extracted with ethyl acetate and washed with 1000 mL water and 1000 mL brine. After drying, and removal of the solvent, 137 g (89.5% yield) of a very viscous oil resulted.

EXAMPLE 1

N-(2-(4-Chlorophenyl)-2-[(1,2,4-triazol-1-yl)methyl]-hexyl)formamide

A stirred mixture of 1.09 mL (11.51 mmol) of acetic anhydride and 0.45 mL (10.26 mmol) of 88% formic acid was heated to 50° C. under nitrogen for 2 hours. The resultant solution was cooled to 0° C. and a solution of 1.0 g (3.42 mmol) of 2-(4-chlorophenyl)-2-[(1,2,4-triazol-1-yl)methyl]-2-hexylamine, in 3 mL of tetrahydrofuran was added. This mixture was allowed to warm to room temperature and was stirred for 24 hours. The solution was poured into ice-water and extracted with ethyl ether. The combined organic layers were washed with saturated sodium bicarbonate solution (until wash was basic by pH paper), then brine, and dried over magnesium sulfate. Removal of solvents under reduced pressure gave 1.0 g (91%) of the desired formamide as a syrupy oil:

$^1$H-NMR (CDCl$_3$, Me$_4$Si) 0.95 (t, J=6 Hz, CH$_2$—CH$_3$), 1.0–1.5 (m), 1.5–1.8 (m), 3.0–3.75 (m, CH$_2$-NHCHO), 4.35 (s, CH$_2$-N), 7.1 (m, aromatic H), 7.5 (s, CH=N), 7.7 (s, CH=N), 8.1 ppm (br d, NHCHO);

IR (film) 3300, 3140, 3060, 2960, 2940, 1670, 1500, 1380, 1275, 1140, 1010, 960, 830, 680 cm$^{-1}$.

EXAMPLE 2

2-(4-Chlorophenyl)-2-](1,2,4-triazol-1-yl)methyl]hexylisocyanide

To a stirred solution of 0.50 g (1.55 mmols) of N-(2-(4-chlorophenyl)-2-[(1,2,4-triazol-1-yl)methyl]hexyl)-formamide in 5 mL of anhydrous methylene chloride under nitrogen was added 0.44 mL (3.10 mmols) of triethylamine followed by 0.418 g (1.55 mmols) of 3-ethyl-2-chlorobenzoxazolium tetrafluoroborate. After stirring at room temperature for 12 hours the resultant mixture was poured into ice-water and extracted with ethyl acetate. The combined organic layers were washed once with 10% hydrochloric acid, brine, and dried over magnesium sulfate. Removal of solvents at reduced pressure afforded a crude mixture which was chromatographed (Merck ® 60 silica gel, 50% ethyl acetate-hexane) to give 0.300 g (64%) of the isocyanide as a clear, colorless oil: $^1$H-NMR (CDCl$_3$, Me$_4$Si) 0.85 (t, J=6 Hz, CH$_2$—CH$_3$), 1.0–1.55 (m), 1.6–1.8 (m), 3.4–4.0 (m, CH$_2$—NC), 4.55 (d, J=5 Hz, CH$_2$-triazole), 4.65 (d, J=12 Hz, CH$_2$-triazole, 7.0–7.4 (m, aromatic H), 7.85 ppm (m, CH=N);

IR (film) 3140, 3080, 2960, 2940, 2880, 2175, 1610, 1480, 1470, 1400, 1270, 1250, 1140, 1010, 920, 830, 740, 680 cm$^{-1}$.

EXAMPLE 3

2-(4-Chlorophenyl)-2-[(1,2,4-triazol-1-yl)methyl]hexanal

To a stirred solution of 0.410 g (4.1 mmols) of chromium trioxide in 10 mL of methylene chloride was added 0.65 mL (8.2 mmols) of pyridine. After the resultant mixture turned from yellow to burgundy in color (about 15 minutes), 0.200 g (0.7 mmol) of 2-(4-chlorophenyl) 2-[(1,2,4-triazol-1-yl)methyl]hexan-1-ol was added. After 30 minutes the supernatant solution was decanted and the residue was washed twice with ether. The combined organic layers were washed three times with 5% sodium hydroxide, twice with 5% hydrochloric acid, 5% sodium bicarbonate, brine, and dried over magnesium sulfate. Removal of solvents under reduced pressure gave a pale yellow oil. Residual pyridine was removed under full vacuum to give 0.12 g (63%) of aldehyde as a viscous oil: $^1$H-NMR (CDCl$_3$, Me$_4$Si) 0.9–1.1 (t, J=6 Hz, CH$_2$—CH$_3$), 1.3–1.6 (m), 1.8–2.3 (m), 4.65 (s, CH$_2$—N), 7.2 (ABq,=20.5 Hz, J$_{AB}$=8 Hz, phenyl H), 7.5 (s, CH=N), 7.8 (s, CH=N), 9.5 ppm (s, CHO);

IR (film) 3100, 2940, 2900, 3840, 1700, 1575, 1475, 1260, 1195, 1125, 1080, 1000, 820, 745, 665 cm$^{-1}$.

EXAMPLE 4

3-(4-Chlorophenyl)-3-[(1,2,4-triazol-1-yl)methyl]-1-heptene

To a stirred solution of 1.64 g (4.6 mmol) of methyltriphenylphosphonium bromide in 25 mL of tetrahydrofuran was added, dropwise, 3.0 mL (4.2 mmols) of a 1.4M n-butyllithium-hexane solution. After 2 hours, a solution of 1.22 g (4.2 mmols) of 2-(4-chlorophenyl)-2-[(1,2,4-triazol-1-yl)methyl]hexanal in 5 mL of tetrahydrofuran was added and the resultant mixture was heated to reflux for 48 hours. The reaction was quenched with the addition of ice and the product was isolated with methylene chloride. Removal of solvents under reduced pressure and chromatography (Merck ®

60 silica gel, 50% ethyl acetate-hexane) afforded 0.520 g (43%) of the olefin as a clear, colorless oil: :$^1$H-NMR (CDCl$_3$, Me$_4$Si) 0.8–1.1 (t, J=6 Hz, CH$_2$—CH$_3$), 1.2–1.7 (m), 1.75–2.1 (m), 4.6 (s, CH$_2$—N), 5.0–6.4(m,BH=CH$_2$),7.1–7.3 (m,phenyl H), 7.5 (s,CH=N), 7.9 ppm (s,CH=N);

IR (film) 3080, 2950, 2850, 1650, 1480, 1450, 1265, 1130, 1090, 1010, 950, 920, 830, 680 cm$^{-1}$.

EXAMPLE 5

2-(4-Chlorophenyl)-2-[(1,2,4-triazol-1-yl)methyl]hexanoylazide

To a stirred solution of 1.0 g (3.25 mmols) of 2-(4-chlorophenyl)-2-[(1,2,4-triazol-1-yl)methyl]hexanoic acid in 3 mL of dimethylformamide was added 0.30 mL of tert-butanol. This solution was cooled to 0° C. and a solution of 1.07 g (3.90 mmols) of diphenylphosphorylazide in 1 mL of dimethylformamide was added followed by 0.72 mL (7.15 mmols) of triethylamine. The resultant mixture was stirred for 2 hours and then allowed to warm to room temperature and stirred for an additional 15 hours. Addition of ice caused the precipitation of the product. Filtration gave 1.10 g of a crude product which was carefully recrystallized from a 1 to 3 mixture of ethyl acetate and hexane to afford 0.46 g (47%) of azide as a white crystalline solid, melting point 100°–101° C.: $^1$H-NMR (CDCl$_3$, Me$_4$Si) 0.7–1.1 (t, J=6 Hz, CH$_2$—CH$_3$), 1.1–1.7 (m), 1.75–2.1 (m), 4.6 (d, CH$_2$—N), 6.8–7.2(m,phenyl H), 7.3 (s,CH=N), 7.7 ppm (s,CH=N):

$^{13}$C-NMR (CDCl$_3$) 181.4, 151,7, 144.0, 137.0, 134.5 129.3, 127.9, 56.3, 53.2, 31,7, 26.3, 23.0, 13.8 ppm.

IR 3025, 2975, 2140, 1695, 1490, 1270, 1215, 1180, 1010, 670 cm$^{-1}$.

EXAMPLE 6

2-(4-Chlorophenyl)-(E,Z)-1-hydroxyamino-2-[(1,2,4-triazol-1-yl)methyl]hexanal

To a stirred solution of 1.20 g (4.1 mmols) of 2-(4-chlorophenyl)-2-[(1,2,4-triazol-1-yl)methyl]hexanal in 4 mL of ethanol was added 0.360 g (5.13 mmols) of hydroxylamine hydrochloride. This mixture was heated to reflux and 0.27 g (2.56 mmol) of sodium carbonate in 1 mL of water was added. After an additional 15 hours at reflux the mixture was poured into ice-water, saturated with sodium chloride, and extracted with ethyl acetate. The organic layer was washed once with water, brine, and dried over magnesium sulfate. Removal of solvents at reduced pressure afforded 1.1 g (87%) of the oxime as a white solid, melting point 127°–33° C.:: $^1$H-NMR (CDCl$_3$, Me$_4$Si) 0.6–1.0(t,J=6 Hz, CH$_2$—C$_H$3), 1.1–1.6 (m), 1.7–2.1 (m), 4.7 (d,CH$_2$—N), 7.2(ABq,=13.8 Hz, J$_{AB}$=8 Hz, phenyl H), 7.6 (s, CH=N), 7.9 (S, CH=N), 10.95 ppm (br s, —OH).

EXAMPLE 7

2-(4-Chlorophenyl)-1-(1,2,4-triazol-1-yl)-2-hexylamine

To a stirred solution of 1.0 g (3.25 mmols) of 2-(4-chlorophenyl)-2-[(1,2,4-triazol-1-yl)methyl]hexanoic acid in 10 mL of tert-butanol was added 0.87 mL (3.25 mmols) of diphenylphosphorylazide followed by 0.33 mL of triethylamine. This mixture was heated to reflux for 48 hours. The tert-butanol was removed under reduced pressure and the residue was taken up in 5% hydrochloric acid and washed with ethyl acetate. The acidic aqueous layer was made basic with concentrated ammonium hydroxide and extracted with ethyl acetate. Removal of solvents from the organic extract afforded 0.510 g (57%) of the amine as a viscous oil: $^1$H-NMR (CDCl$_3$, Me$_4$Si) 0.8–1.2 (t,J=6 Hz, CH$_2$—CH$_3$), 1.2–1.7 (m), 1.7–2.2 (m), 2.0 (br s, —NH$_2$), 4.6 (s, CH$_2$—N), 7.45 (s, phenyl H), 7.8 (s, CH=N), 8.0 ppm (s, CH=N);

IR (film) 3350, 3260, 2925, 1650, 1570, 1470, 1250, 1180, 1120, 1070, 990, 810 cm$^{-1}$.

EXAMPLE 8

N-[2-(4-Chlorophenyl)-1-(1,2,4-triazol-1-yl)-2-hexyl]-formamide

A mixture of 0.68 mL (7.2 mmols) of acetic anhydride and 0.28 mL (6.42 mmols) of 88% formic acid was heated to 50° C. for 2 hours under nitrogen. The resultant solution was cooled to 0° C. and a solution of 0.600 g (2.14 mmol) of 2-(4-chlorophenyl)-1-(1,2,4-triazol-1-yl)-2-hexylamine in 2 mL of tetrahydrofuran was added. This mixture was allowed to warm to room temperature and stir for 48 hours. The resultant solution was poured into ice-water and extracted with ethyl acetate. The aqueous layer was saturated with sodium chloride and extracted with ethyl acetate. The combined organic layers were washed with saturated sodium bicarbonate, brine, and dried over magnesium sulfate. Removal of solvents under reduced pressure gave a foam. Recrystallization from ethyl acetate-hexane gave 0.35 g (53%) of the amide as a white crystalline solid, melting point 129°–31° C.: $^1$H-NMR (CDCl$_3$, Me$_4$Si) 0.8 (t, J=6 Hz, CH$_2$—CH$_3$), 1.0–1.5 (m), 1.7–2.0 (m), 4.95 (br d, CH$_2$—N), 7.3 (m, phenyl H), 7.95 (br s, CH=N), 8.2 (br d, —NCHO), 9.9 ppm (br s, NHCHO);

IR 3300, 3150, 3050, 2980, 2950, 2880, 1680, 1490, 1280, 1140, 1100, 1015, 840, 680 cm$^{-1}$.

EXAMPLE 9

2-(4-Chlorophenyl)-1-(1,2,4-triazol-1-yl)-2-hexylisocyanide

To a stirred solution of 0.40 g (1.3 mmols) of N-[2-(4-chlorophenyl)-1-(1,2,4-triazol-1-yl)-2-hexyl]formamide in 5 mL of methylene chloride under nitrogen was added 0.45 mL (3.26 mmols) of triethylamine. To this mixture was added a slurry of 0.439 g (1.63 mmols) of 3-ethyl-2-chlorobenzoxazolium tetrafluoroborate, which was weighed out under a nitrogen atmosphere, in 5 mL of methylene chloride. The reaction mixture was then allowed to stir at room temperature for 12 hours. The reaction mixture was poured into ice water and extracted with ethyl acetate. The combined organic layers were washed once with 10% hydrochloric acid, brine, and dried over magnesium sulfate. Removal of solvents gave a crude oil which was purified by column chromatography (Merck 60 silica gel, ethyl acetate/-hexane) to give 0.20 g (52%) of a clear, colorless oil.

$^1$H-NMR 200 MHz (CDCl$_3$, Me$_4$Si) 0.8 (t, J=5 Hz, CH$_2$—CH$_3$), 1.0–1.6 (m, 4H, 1.90–2.2 (m, 2H), 4.55 (ABq, J=16.8 Hz, J$_{AB}$=15 Hz, CH$_2$—N), 7.2–7.5 (q, 4H, aromatic H), 7.9 (s, CH=N), 8.0 ppm (s, CH=N).

EXAMPLE 10

N-[2-(4-Chlorophenyl)-1-(1,2,4-triazol-1-yl)-2-hexyl]acetamide

To a stirred, cooled (0° C.) solution of 0.54 g (1.94 mmols) of [2-(4-chlorophenyl)-1-(1,2,4-triazol-1-yl)-2-hexylamine and 0.02 g (0.15 mmols) of N,N-dimethylaminopyridine in 10 mL of methylene chloride under nitrogen was added dropwise 0.50 mL (5.28 mmols) of acetic anhydride. After 5 days the reaction was quenched with the addition of methanol and the solvents were removed to give a white solid. The solid was dissolved in toluene which was removed under reduced pressure to remove any acetic acid. The resultant solid was recrystallized from chloroform to give 0.2 g (32%) of white crystals, melting point 178.5°-179° C.

$^1$H-NMR 200 MHz (CDCl$_3$, Me$_4$Si) 0.85 (t, J=7.5 Hz, CH$_2$—CH$_3$), 1.0–1.4 (m, 4H), 1.8–2.2 (m, 2H), 2.05 (s, COCH$_3$), 4.85 (ABq, J=35.3 Hz, J$_{AB}$=12.5 Hz, CH$_2$—N), 5.95 (s, NH), 7.05–7.4 (q, aromatic H), 7.8 (s, CH=N), 7.95 ppm (s, CH=N).

EXAMPLE 11

The compounds of Examples 1–10 of this invention were tested for fungicidal activity in vivo against wheat powdery mildew (WPM), wheat stem rust (WSR), rice blast (RB), rice sheath blight (RSB), and cucumber downy mildew (CDM). In tests on cereals (except rice plants used for testing rice blast), the plants were trimmed about 24 hours prior to the application of the fungicide compound to provide a uniform plant height and to facilitate uniform application of the compound and inoculation with the fungus. The compounds were dissolved in a 2:1:1 mixture of water, acetone and methanol, sprayed onto the plants, allowed to dry (four to six hours) and then the plants were inoculated with the fungus. Each test utilized control plants which were sprayed with the water, acetone and methanol mixture and inoculated with the fungus. The remainder of the technique of each of the tests is given below and the results are reported in Table 1 as percent disease control (percentages of plants treated with the compounds of the present invention lacking disease signs or symptoms compared to the untreated control plants).

Wheat Powdery Mildew (WPM)

*Erysiphe graminis* (f. sp. *tritici*) was cultured on Pennol wheat seedlings in a controlled temperature room at 65° to 70° F. Mildew spores were shaken from the culture plants onto Pennol wheat seedlings which had been previously sprayed with the fungicide compound. The inoculated seedlings were kept in a controlled temperature room at 65° to 75° F. and subirrigated. The percent disease control was rated 8 to 10 days after the inoculation.

Wheat Stem Rust (WSR)

*Puccinia graminis* (f. sp. *tritici* Race 15B-2) was cultured on Wanzer wheat seedlings for a period of 14 days in a greenhouse. A water suspension of the spores from infested plants was obtained and the spore concentration was adjusted to about 2×10$^5$ spores per ml of deionized water. Wanzer wheat plants which had been previously treated with the fungicide compounds were inoculated by applying the stem rust spore suspension, until runoff, with a DeVilbiss atomizer at 5 lbs. per square inch air pressure. After inoculation, the plants were placed in a humid environment at approximately 75° F. where they were exposed to 12 hours of continuous darkness followed by a minimum of 3 to 4 hours of light having an intensity of about 500 footcandles. The temperature in the chamber did not exceed 85° F. At the end of the light period, the plants were placed in a greenhouse where they were permitted to grow for a period of two weeks at which time the percent disease control was determined.

Rice Blast (RB)

Nato rice plants were inoculated with *Piricularia oryzae* (about 20,000 conidia per ml) by spraying the leaves and stems with an airbrush until a uniform film of inoculum was observed on the leaves. The inoculated plants were incubated in a humid environment (75° to 85° F.) for about 24 hours, then placed in a greenhouse environment (70° to 75° F.). Seven to eight days after inoculation, the percent disease control was determined.

Rice Sheath Blight (RSB)

*Pellicularia filamentosa* f. sp. *sasiki* was cultured on an autoclaved mixture of crushed rice seeds and potato dextrose broth (100 g of rice seeds per 30 ml of potato dextrose broth) in a 500 ml Erlenmeyer flask. After 10 days, the culture was blended in a blender to produce a uniform inoculum. Approximately one teaspoon of inoculum was spread among Lebonnet rice seedlings on the soil surface of each pot (3 inch diameter). The inoculated seedlings were incubated for five days in a humidity cabinet (85° to 90° F.). Percent disease controls were determined immediately after removing the seedlings from the cabinet.

Cucumber Downy Mildew (CDM)

*Pseudoperonospora cubensis* was maintained on leaves of live Marketeer cucumber plants in a constant temperature room at 65° to 75° F. in humid air with moderate light intensity for 7 to 8 days. A water suspension of the spores from infested leaves was obtained and the spore concentration was adjusted to about 1×10$^5$ per ml of water. Marketeer cucumber seedlings were inoculated by spraying the underside of the leaves with a DeVilbiss atomizer until small droplets were observed on the leaves. The inoculated plants were incubated in a mist chamber for 24 hours at about 70° F. and then subsequently incubated for 6 to 7 days in a controlled temperature room under mist at 65° to 75° F. Seven days after inoculation, the percent disease control was determined.

TABLE 1

% Control at 200 ppm of the 1,2,4-triazoles Versus Assorted Fungi

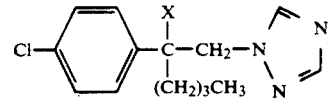

| Example | X | WPM[1] | WSR[2] | RB[3] | RSB[4] | CDM[5] |
|---|---|---|---|---|---|---|
| 1 | —CH$_2$NHCHO | 80 | 0 | 0 | 0 | 0 |
| 2 | —CH$_2$N≡C | 80 | 100 | 0 | 0 | 0 |
| 3 | —CHO | 100 | 100 | 70 | 50 | 0 |
| 4 | —CH=CH$_2$ | 100 | 100 | 80 | 60 | 80 |
| 5 | —CON$_3$ | 100 | 70 | —[6] | 0 | 20 |
| 6 | —CH=N—OH | 100 | 100 | 0 | 0 | 0 |
| 8 | —NHCHO | 100 | 60 | 0 | — | 0 |
| 9 | —N≡C | 100 | 90 | 80 | 0 | 0 |
| 10 | —NHCOCH$_3$ | 30 | 0 | 0 | 70 | 0 |

[1] Wheat powdery mildew
[2] Wheat stem rust
[3] Rice blast
[4] Rice sheath blight
[5] Cucumber downy mildew
[6] — is not tested The 1,2,4-triazoles, and the enantiomorphs, acid addition salts and metal salt complexes thereof are useful as agricultural fungicides and as such can be applied to various loci such as the seed, the soil or the foliage. For such purposes these compounds can be used in the technical or pure form as prepared, as solutions or as formulations. The compounds are usually taken up in a carrier or are formulated so as to render them suitable for subsequent dissemination as fungicides. For example, these chemical agents can be formulated as wettable powders, emulsifiable concentrates, dusts, granular formulations, aerosols, or flowable emulsion concentrates. In such formulations, the compounds are extended with a liquid or solid carrier and, when desired, suitable surfactants are incorporated.

It is usually desirable, particularly in the case of foliar spray formulations, to include adjuvants, such as wetting agents, spreading agents, dispersing agents, stickers, adhesive and the like in accordance with agricultural practices. Such adjuvants commonly used in the art can be found in the John W. McCutcheon, Inc. publication "Detergents and Emulsifiers, Annual."

In general, the compounds of this invention can be dissolved in certain solvents such as acetone, methanol, ethanol, dimethyl-formamide, pyridine or dimethyl sulfoxide and such solutions can be diluted with water. The concentrations of the solution can vary from about 1% to about 90% with a preferred range being from about 5% to about 50%.

For the preparation of emulsifiable concentrates, the compound can be dissolved in suitable organic solvents, or a mixture of solvents, together with an emulsifying agent which permits dispersion of the fungicide in water. The concentration of the active ingredient in emulsifiable concentrates is usually from about 10% to about 90%, and in flowable emulsion concentrates, can be as high as about 75%.

Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of from about 20% to about 98%, preferably from about 40% to about 75%. A typical wettable powder is made by blending 50 parts of a 1,2,4-triazole, 45 parts of a synthetic precipitated hydrated silicon dioxide sold under the trademark Hi-Sil ®, and 5 parts of sodium lignosulfonate. In another preparation a kaolin type (Barden) clay is used in place of the Hi-Sil ® in the above wettable powder, and in another such preparation 25% of the Hi-Sil ® is replaced with a synthetic sodium silico aluminate sold under the trademark Zeolex ®7.

Dusts are prepared by mixing the 1,2,4-triazoles, or the enantiomorphs, salts and complexes thereof with finely divided inert solids which can be organic or inorganic in nature. Materials useful for this purpose include botanical flours, silicas, silicates, carbonates and clays. One convenient method of preparing a dust is to dilute a wettable powder with a finely divided carrier. Dust concentrates containing from about 20% to about 80% of the active ingredient are commonly made and are subsequently diluted to from about 1% to about 10% use concentration.

The 1,2,4-triazoles, and the enantiomorphs, salts and complexes thereof can be applied as fungicidal sprays by methods commonly employed, such as conventional high-gallonage hydraulic sprays, low-gallonage sprays, air-blast spray, aerial sprays and dusts. The dilution and rate of application will depend upon the type of equipment employed, the method of application, plants to be treated and diseases to be controlled. Generally, the compounds of this invention will be applied in an amount of from about 0.01 pound to about 20 pounds per acre of the active ingredient.

As a seed protectant, the amount of toxicant coated on the seed is usually at a dosage rate of from about 0.05 to about 20, preferably from about 0.05 to about 4, and more preferably from about 0.1 to about 1 ounce per hundred pounds of seed. As a soil fungicide the chemical can be incorporated in the soil or applied to the surface usually at a rate of from about 0.02 to about 20, preferably from about 0.05 to about 10 and more preferably from about 0.1 to about 5 pounds per acre. As a foliar fungicide, the toxicant is usually applied to growing plants at a rate of from about 0.01 to about 10, preferably from about 0.02 to about 5 and more preferably from about 0.25 to about 1 pound per acre.

Fungicides which can be combined with the fungicides of this invention include:

(a) dithiocarbamate and derivatives such as: ferbam, ziram, maneb, mancozeb, zineb, propineb, metham, thiram, the complex of zineb and polyethylene thiuram disulfide, dazomet, and mixtures of these with copper salts;

(b) nitrophenol derivatives such as: dinocap, binapacryl, and 2-sec-butyl-4,6-dinitrophenyl isopropyl carbonate;

(c) heterocyclic structures such as: captan, folpet, glyodine, anilazine, ditalimfos, 4-butyl-1,2,4-triazole, 5-amino-1-[bis(dimethylamino)phosphinyl]-3-phenyl-1,2,4-triazole, etradiazole, dithianon, thioquinox, benomyl, thiabendazole, 4-(2-chlorophenylhydrazono)-3-methyl-5-isoxazolone, vinclozolin, iprodione, procymidone, triadimenol, triadimefon, bitertanol, prochloraz, fenarimol, bis-(p-chlorophenyl)-3-pyridinemethanol, bis-(p-chlorophenyl)-5-pyrimidinemethanol, triarimol, flutriafol, flusilazole, propiconazole, ectaconazole, myclobutanil, alpha-[2-(4-chlorophenyl)ethyl]-alpha-phenyl-1H-1,2,4-triazole-1-propanenitrile, hexaconazole, cyproconazole, tebuconazole, diniconazole, fluoroimide, pyridine-2-thiol-1-oxide, 8-hydroxyquinoline sulfate and metal salts thereof, 2,3-dihydro-5-carboxanilido-6-methyl-1,4-oxathiin-4,4-dioxide, 2,3-dihydro-5-carboxanilido-6-methyl-1,4-oxathiin, cis-N-[(1,1,2,2-tetrachloroethyl)thiol]-4-cyclohexene-1,2-dicarboximide, cycloheximide, dehydroacetic acid, captafol, ethirimol, quinomethionate, D,L-methyl-N-(2,6-dimethylphenyl)-N-(2'-methoxyacetyl)alanine methyl ester, D,L-methyl-N-(2,6-dimethylphenyl)-N-chloroacetyl-D,L-2-aminobutyrolactone, D,L-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-(3,5-dichlorophenyl)-5-methyl-5-(methoxymethyl)-1,3-oxazolidi-2,4-dione, 3-(3,5-dichlorophenyl)-1-isopropylcarbamoylhydantoin, 2-cyano-[N-(ethylaminocarbonyl)-2-methoximino]acetamide, fenpropimorph, fenpropidine, 2,6-dimethyl-N-tridecylmorpholine, dodemorph, and triforine;

(d) miscellaneous halogenated fungicides such as: chloranil, dichlone, chloroneb, tricamba, TCPN, dichloran, 2-chloro-1-nitropropane, polychloronitrobenzenes such as pentachloronitrobenzene (PCNB), and tetrafluorodichloroacetone;

(e) fungicidal antibiotics such as: griseofulvin, kasugamycin, polyoxin, validamycin, and streptomycin;

(f) copper-based fungicides such as: copper hydroxide, cuprous oxide, basic cupric chloride, basic copper carbonate, copper terephthalate, copper naphthenate and Bordeaux mixture; and (g) miscellaneous fungicides such as: dodine, phenylmercuric acetate, N-ethylmercuri-1,2,3,6-tetrahydro-3,6-endomethano-3,4,5,6,7,7-hexachlorophthalimide, phenylmercuric monoethanol ammonium lactate, p-dimethylaminobenzene sodium sulfonate, methyl isothiocyanate, 1-thiocyano-2,4-dinitrobenzene, 1-phenylthiosemicarbazide, nickel-containing compounds, calcium cyanamide, lime sulfur, thiophanate-methyl, flutolanil, edinophos, isoprothiolane, propenazole, and tricyclazole.

The 1,2,4-triazoles, and the enantiomorphs, acid addition salts and metal salt complexes thereof can be advantageously employed in various ways. Since these compounds possess broad spectrum fungicidal activity, they can be employed in the storage of cereal grain. These complexes can be employed as fungicides in cereals including wheat, barley, and rye in rice, peanuts, beans, grapes, on turf, in fruit, nut, and vegetable orchards, and in golf course applications. Examples of diseases against which the compounds of the invention are useful include helminthosporium of corn and barley, wheat and barley powdery mildew, wheat leaf and stem rusts, tomato early blight, tomato late blight, peanut early leaf spot, grape powdery mildew, grape black rot, apple scab, apple powdery mildew, cucumber powdery mildew, brown rot of fruits, botrytis, bean powdery mildew, cucumber anthracnose, wheat septoria nodorum, rice sheath blight and rice blast.

Other applications of the 1,2,4-triazoles of this invention will suggest themselves to those skilled in the art of agriculture.

We claim:

1. A compound of the formula

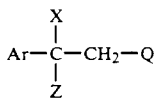

wherein

Ar is phenyl, naphthyl, or phenyl or naphthyl each independently substituted with up to three substituents independently selected from the group consisting of halogen, trihalomethyl, cyano, phenyl, phenoxy, $(C_1-C_4)$alkyl, halo$(C_1-C_4)$alkyl, $(C_1-C_4)$alkoxy and halo$(C_1-C_4)$alkoxy;

Z is $(C_2-C_{12})$alkyl, halo$(C_1-C_{12})$alkyl, cyclo$(C_3-C_8)$alkyl, cyclo$(C_3-C_8)$alkyl$(C_1-C_5)$alkyl, $(C_6-C_{10})$aryl, $(C_6-C_{10})$ar$(C_1-C_5)$alkyl, or $(C_6-C_{10})$aryl or $(C_6-C_{10})$ar$(C_1-C_5)$alkyl each independently substituted with up to three substituents independently selected from the group consisting of halogen, trihalomethyl, cyano, phenyl, phenoxy, $(C_1-C_4)$alkyl, halo$(C_1-C_4)$alkyl, $(C_1-C_4)$alkoxy and halo$(C_1-C_4)$alkoxy;

Q is a 1-(1,2,4-triazolyl) or a 4-(1,2,4-triazolyl); and

X is —NC, —CH$_2$N≡C, —CH$_2$NHCHO, —NHCHO, —NHCOCH$_3$, —NHCO$_2$R, —NHCONHR, —NH$_2$, —N=C(R)$_2$, —NCO or —NO$_2$ wherein R is H or $(C_1-C_5)$alkyl; or the agronomically acceptable enantiomorphs, acid addition salts, or metal salt complexes thereof.

2. The compound of claim 1 in which Ar is phenyl or phenyl substituted with up to three substituents independently selected from halo, trihalomethyl, cyano, $(C_1-C_4)$alkyl, $(C_1-C_4)$alkoxy, or phenyl;

Z is selected from $(C_2-C_{12})$alkyl, $(C_1C_{12})$haloalkyl, $(C_3-C_8)$cycloalkyl, $(C_3-C_8)$cycloalkyl$(C_1-C_5)$alkyl, substituted phenyl, benzyl or phenethyl, or phenyl, benzyl or phenethyl the aromatic ring of which is substituted with up to two halo atoms or trihalomethyl; Q is an unsubstituted 1-(1,2,4-triazole) and R is H or $(C_1-C_4)$alkyl.

3. The compound of claim 2 wherein Ar is phenyl or phenyl substituted at the 4-position with chloro, bromo, fluoro, or trifluoromethyl; Z is ($C_2$ to $C_6$)alkyl, phenyl, benzyl or phenethyl, or monochloro substituted phenyl, benzyl or phenethyl and R is H.

4. The compound of claim 3 wherein Z is $(C_2-C_6)$alkyl.

5. The compound of claim 4 wherein X is selected from —N≡C, —CH$_2$N≡C, —CH$_2$NHCHO, —NHCHO, —NH$_2$, and —NHCOCH$_3$.

6. The compound of claim 5 which is 2-(4-chlorophenyl)-1-(1,2,4-triazol-1-yl)-2-hexylisocyanide.

7. The compound of claim 5 which is 2-(4-chlorophenyl)-2-[(1,2,4-triazol-1-yl)methyl]hexylisocyanide.

8. The compound of claim 5 which is 2-(4-chlorophenyl)-1-(1,2,4-triazol-1-yl)-2-hexylamine.

9. A fungicidal composition which comprises an agronomically acceptable carrier and a fungicidally effective amount of a compound of claim 1.

10. A method for controlling fungi which consists of applying to the locus where control is desired a fungicidally effective amount of a compound of claim 1.

* * * * *